United States Patent [19]

LeBlanc, Jr.

[11] Patent Number: 4,634,501

[45] Date of Patent: Jan. 6, 1987

[54] ARTICLE AND METHOD FOR DETERMINING THE CONCENTRATION OF METAL IONIC COMPLEXES IN A SOLUTION

[75] Inventor: Oliver H. LeBlanc, Jr., Schenectady, N.Y.

[73] Assignee: General Electric Company, Schenectady, N.Y.

[21] Appl. No.: 857,217

[22] Filed: Apr. 29, 1986

[51] Int. Cl.$^4$ .................... G01N 27/30; G01N 27/58
[52] U.S. Cl. .................................... 204/1 T; 204/418
[58] Field of Search ........................ 204/418, 1 T, 296

[56] References Cited

U.S. PATENT DOCUMENTS 3,419,634 12/1968 Vaughn et al. .................. 260/824
3,743,588 7/1973 Brown et al. .................. 204/418 X
3,767,553 10/1973 Brown et al. .................. 204/418

OTHER PUBLICATIONS

LeBlanc, Jr. et al., *Long-Lived Potassium Ion–Selective Polymer Membrane Electrode*, Analytical Chemistry, vol. 48, p. 1658, Oct., 1976 (reprint).
Golubev et al., *Liquid Ion–Selective Electrodes Based on Ionic Associates of Dyes with Anionic Complexes*, J. Analytical Chemistry USSR 38, pp. 1536–1538, 1983.
Zarinskii et al., *Second Symposium on Ion–Selective Electrodes*, 1976, E. Pungor and I. Buzas, editors, (pub. 1977), pp. 245–253 [Chem. Abst. 88,98595n (1978)], "New Liquid State Membrane Electrodes for Rhenium(VII) and Gold(I,III) Based on Ion-Associated Systems".
Avdeeva et al., Anal. Khim. 37, 1434–1440 (1982) (Russ) [Chem. Abst. 98, 45987s], "Plasticized Ion-Selective Electrodes for Determination of Gold in Chloride and Cyanide Solutions", J. Anal. Chem. USSR 37, 1102–1107 (1983).
Bychkov et al., Liquid Ion–Selective Electrode for Determining Gold in Cyanide Solutions, Zh. Anal. Khim. 1976, 31(11), 2114–2119 (Russ.), Chem. Abstracts 86, 1823439f (1977).
Gordievskii et al., *Composition of Ion–Selective Electrode Membrane for Determination of Dicyanoaurate Ions*, USSR SU 957,086, Dec. 3, 1980; Chem. Abs. 98, 136829h (1983).
Bychkov et al., *Liquid Ion–Selective Electrodes Based on Ion Associates and Metal–Containing Anions*, Deposited Doc. 1977, VINITI 3564-77, 29 pages, (Russ.); Chem. Abs. 90, 194625j; (1979).
Borovskii et al., *Dicyanoaurate (I) Anion–Selective Electrode for Rapid Determination of Gold and in Automated Technological Monitoring*, Zavod Lab. 1982, 48 (12), 20–2 (Russ.), Chem. Abs. 98, 100321x (1983).
Golubev et al., *Effect of Extraction Characteristics of the System Electrolyte–Liquid Membrane on the Electrode Function of a Dicyanoaurate (I) Electrode*, Latv. PSR Zinat. Akad. Vestis Kim. Ser. 1983, (1), 45–7 (Russ.); Chem. Abs. 98, 151672v (1983).

*Primary Examiner*—G. L. Kaplan
*Attorney, Agent, or Firm*—Francis T. Coppa; James C. Davis, Jr.; James Magee, Jr.

[57] ABSTRACT

A device and method for determining the concentration of dicyanoaurate anions in a solution is disclosed. The device includes a semipermeable membrane formed from a material permeable to dicyanoaurate anions. The material may be comprised of an organopolysiloxane-polycarbonate block copolymer and a complexed salt of the dicyanoaurate anion.

8 Claims, 4 Drawing Figures

ARTICLE AND METHOD FOR DETERMINING THE CONCENTRATION OF METAL IONIC COMPLEXES IN A SOLUTION

BACKGROUND OF THE INVENTION

This invention relates to methods and apparatus for measuring the concentration of specific ions in aqueous solutions, and more particularly to a membrane-containing sensor device for determining the concentration of dicyanoaurate anions in an electroless plating bath.

Ion-specific sensor devices for determining the concentration of various ionic species are known in the art. For example, Bychkov et al describes ion-selective electrodes for determining gold in cyanide solutions (Journal of Analytical Chemistry of the U.S.S.R., 31(a), (1976) pages 1543–1547). The membranes of Bychkov et al are liquid solutions of the ionic associate of tetraphenylarsonium and the dicyanoaurate ion $(C_6H_5)_4As^+Au(CN)^-_2$ in various organic solvents. However, liquid membranes have several disadvantages. For example, they often take the form of very complicated structures which have to be constantly replenished with fluids, thereby making them impractical for many large-scale industrial applications.

Solid membranes based on poly(vinyl chloride) (PVC) have been prepared for use in the past as ion selective membranes. However, these types of membranes are plasticized and lack the ruggedness and durability required for many long-term, large-scale industrial plating processes.

A different type of solid ion-specific membrane is described in U.S. Pat. No. 3,743,588, issued July 3, 1973 to Brown et al. The membrane of Brown et al is used for biomedical applications and include a hydrophobic elastomeric polymer and a hydrogen ion-carrier which is an uncoupler known to uncouple oxidative phosphorylation in mitochondria and chloroplasts. Similarly, U.S. Pat. No. 3,767,553, issued Oct. 23, 1973 to Brown et al, discloses a potassium ion-specific membrane comprising a mixture of a hydrophobic elastomeric polymer and a potassium ion-specific carrier. However, the prior art fails to describe or contemplate the use of such solid membranes to determine the concentration of dicyanoaurate anions (hereinafter also referred to as $Au(CN)^-_2$ anions) in gold-containing solutions.

It is therefore an object of this invention to provide an improved membrane for determining the concentration of dicyanoaurate anions in a solution.

An additional object of the present invention is to provide an ion-selective membrane which is not substantially affected by electrical interference.

Yet another object of the present invention is to provide a durable, practical electrolytic device for determining the concentration of dicyanoaurate anions in an electroless gold plating bath.

It is still another object of this invention to provide an improved method for determining the concentration of dicyanoaurate anions in a gold plating bath.

These and other objects of the invention, together with the features and advantages thereof, will become apparent from the following description of the invention.

SUMMARY OF THE INVENTION

The foregoing objects are achieved by a sensor device for determining the concentration of dicyanoaurate anions in an aqueous solution. The device includes a reservoir containing the solution to be tested having immersed therein an electrode. The solution to be tested is separated from a second solution, i.e., a reference solution, by a membrane. The reference solution has a known concentration of dicyanoaurate anions contained therein and having immersed therein a reference electrode. The electrodes are connected through a potential measuring means. The membrane comprises a hydrophobic film permeable to dicyanoaurate anions. Materials suitable for forming the membrane film include elastomeric polymers such as polyurethanes, chloroprene polymers, and vinylidene fluoride-hexafluoropropylene polymers, although it is preferred that the film be formed of an organopolysiloxane polycarbonate block copolymer. The organopolysiloxane-polycarbonate block copolymer has a complexed salt of the dicyanoaurate anion contained therein, and has a dielectric constant of from about 4 to about 13. The membrane functions as an electrically conductive selective barrier between the two solutions. The difference between the potentials of the two electrodes is a measure of the potential difference across the membrane.

The method of the present invention for determining the concentration of dicyanoaurate anions in a sample solution comprises measuring the potential between the electrode in contact with the first solution and the reference electrode in contact with the reference solution, the solutions being separated by the membrane described above. It has now been discovered that the potential difference is proportional to the logarithm of the ratio of the concentration of dicyanoaurate anions in the sample solution to the concentration of dicyanoaurate anions in the reference solution. Determination of the potential difference therefore permits the rapid calculation of the dicyanoaurate anion concentration in the sample solution.

BRIEF DESCRIPTION OF THE DRAWINGS

The apparatus of this invention and the method of its use will be more clearly understood in view of the drawings.

DESCRIPTION OF THE INVENTION

Figure 1:
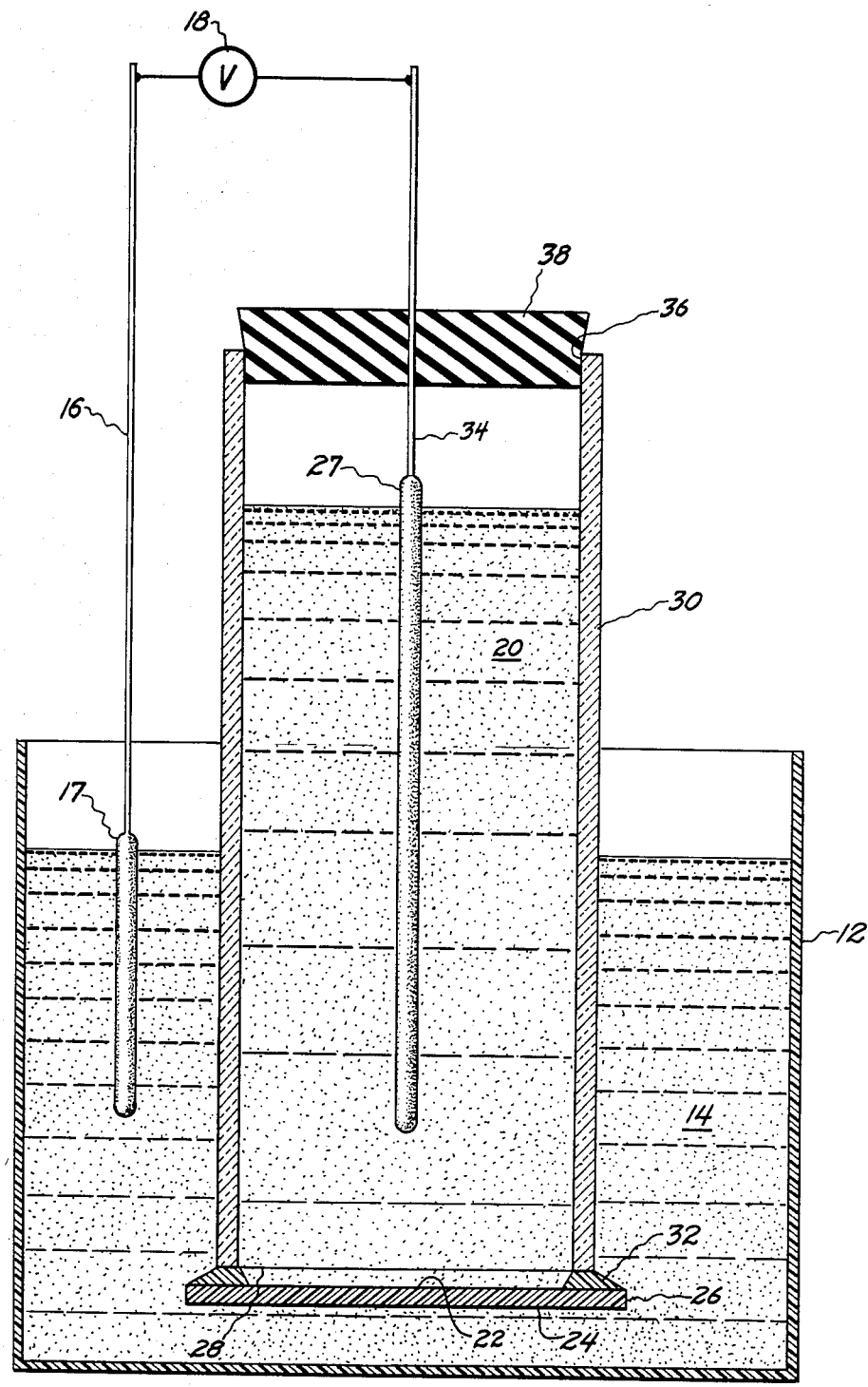
FIG. 1 is a sectional view of an embodiment of the device of the present invention.

The semipermeable membrane of the present invention comprises a film of hydrophobic material. "Semipermeable" as used herein describes a material which is permeable to dicyanoaurate anions but hinders the passage of other substances such as chloride and cyanide ions, as well as metal complexes formed from these ions. If the membrane permeabilities of other ions and complexes are less than about 1.0% of the permeability of the dicyanoaurate ion, then the presence of the other ions or complexes will not adversely affect a determination of the concentration of dicyanoaurate anions.

The material forming the membrane of the present invention is an electrically conductive elastomeric polymer having hydrophobic characteristics which provide stability in aqueous solutions for long periods of time. The preferred materials are organopolysiloxane polycarbonate block copolymers. Such block copolymers are known in the art and are described in U.S. Pat. Nos. 3,419,634, 3,743,588, and 3,767,553, all incorporated by reference herein.

The elastomeric polymer described above, e.g., the organopolysiloxane-polycarbonate block copolymer, has a complexed salt of the dicyanoaurate anion contained therein in the form of a solid solution, optionally including the formation of weak chemical bonds between functional entities of the salt and of the copolymer. The complexed salt functions in part as a cationic extractant which selectively interacts with the cyanide complex of gold(I) against a background of other ions or metal complexes. Preferred complexed salts of the present invention when detecting dicyanoaurate anions are those which include a cationic radical comprising a plurality of phenyl ligands bonded to an electron-accepting atom. Especially preferred cationic radicals are tetraphenyl radicals, and nonlimiting examples of these include tetraphenylphosphonium and tetraphenylarsonium. The anionic component of the salt is typically the particular anion under consideration, e.g., a dicyanoaurate anionic radical for detecting dicyanoaurate anions. Such complexed salts are known in the art and are described, for example, in "Liquid Ion-Selective Electrodes Based on Ionic Associates of Dyes with Anionic Gold Complexes", V. Golubev et al, Journal of Analytical Chemistry, U.S.S.R. 38, 1536–1538 (November 1983). Other complexed salts suitable for the present invention are also described in the Golubev et al article, and include, for example, a salt of the dicyanoaurate anion with the malachite green cation.

The amount of complexed salt in the elastomeric polymer may range from about 0.01% to about 2.0% by weight of the weight of the elastomeric polymer, and an especially preferred amount of salt within that range is about 1.0% by weight. An upper limit for the amount of salt is dictated by its solubility in the polymer. Higher amounts of the salt within the above-described range are generally advantageous because they result in membranes having higher electrical conductivity and consequently exhibiting less electrical interference noise.

Methods of preparing the elastomeric polymers or copolymers of the present invention, e.g., phosgenation, are known in the art and are described, for example, in U.S. Pat. No. 3,419,634, as well as in U.S. Pat. Nos. 3,743,588 and 3,767,553.

The complexed salts of the present invention may also be prepared by methods known in the art. For example, tetraphenylphosphonium dicyanoaurate (hereinafter also referred to as $Ph_4PAu(CN)_2$ may be prepared by dissolving potassium dicyanoaurate, $KAu(CN)_2$, in water, followed by the addition of a slight excess of tetraphenylphosphonium chloride, $Ph_4PCl$. $Ph_4PAu(CN)_2$ immediately precipitates. Excess ionic material is then washed with the precipitate with water, followed by removal of the water through known separation techniques.

The semipermeable membrane of the present invention may be formed by dissolving both the complexed salt and the elastomeric copolymer in a suitable solvent such as methylene chloride, followed by gentle agitation, if necessary, at about 40° C. The resulting mixture may be filtered and concentrated. The membrane is then cast and the solvent removed by methods well-known in the art.

The membrane film resulting from the preparation described above is transparent and rubbery in texture. In contrast to the fragile polyvinylchloride (PVC) membranes of the prior art, the membrane of the present invention exhibits a high level of structural integrity and durability. These properties enable the membrane to be long-lasting, e.g., to have a useful life of greater than 5 years. The durable nature of the membrane is especially useful when the membrane is incorporated into the sensor device of the present invention. For example, when the device is used to determine dicyanoaurate anions in a gold-plating bath, the excellent physical properties of the membrane allow very frequent, uncomplicated and rapid determinations of anion concentrations over the course of many months or years. In marked contrast, prior art systems, e.g., utilization of a liquid membrane, may involve complicated servicing steps to keep the membrane functional, e.g., replenishment of the liquid membrane material. The servicing steps delay the monitoring of dicyanoaurate anions in the bath and thereby reduce the efficiency of the entire gold-plating process because improper levels of the anion may result in undesirable plating rates or poor quality gold deposition.

It will be readily apparent to those skilled in the art that the membrane of the present invention may be modified to allow for the determination of other anions or cations in various solutions. Thus, complexes of gold-(III), silver(I), or Re(II) may be detected (individually) by selecting appropriate complexed metal salts to be dissolved in one of the polymers described above. For example, a membrane selective to potassium-based complexes would include a complexed salt, e.g., here, an anionic extractant such as potassium tetraphenylborate, dissolved in the polymer.

As described above, the semipermeable membrane of the present invention as permeable to dicyanoaurate anions while hindering the passage of other ionic species. In practice, it is not necessary for the dicyanoaurate anions to actually pass through the membrane, as the potential difference across the membrane is measurable when the sample solution is simply in contact with a surface of the membrane, as further described below.

The semipermeable membrane of the present invention forms a part of a device for determining the concentration of dicyanoaurate anions in solution. When the membrane is situated between two aqueous solutions containing different concentrations of dicyanoaurate anions, a potential difference across the membrane is observed, and this potential corresponds closely to the ideal potential difference V predicted by the Nernst equation. The calculation of anion concentration in the sample solution being tested may thus be performed by using the measured potential difference value, as further described below.

One embodiment of the device of the present invention is depicted in FIG. 1, and comprises a reservoir 12 containing therein a sample solution 14 having an unknown concentration of dicyanoaurate anions. Reservoir 12 may be formed from any dielectric material, such as glass, ceramics, plastics, etc. Sample solution 14 should have a pH between about 4 and 11, and may be adjusted to that range by well-known methods, e.g., addition of a basic or acidic species, and the use of a commercial pH buffer. The solution may further contain various other components, depending upon its particular function. For example, when the solution is a gold plating bath, it may include a reducing agent, a buffering agent, alkali metal salts (e.g., potassium chloride), and various other reagents or additives, complexing agents, stabilizers, etc. Sample solution 14 has immersed therein an electrode 16 attached by a connector wire to a pole of an electrode potential-measuring means 18. Electrode 16 may be formed from materials well-known in the art for constructing reference electrodes. For example, as shown in FIG. 1, it may simply be formed from a silver wire having a chlorided terminal portion 17, and in that instance, sample solution 14 must contain a known concentration of chloride ions, e.g., supplied from potassium chloride.

Sample solution 14 is separated from reference solution 20 by membrane film 26, the composition of which is described above. Thus, first surface 22 of membrane 26 is in contact with aqueous solution 20, while second membrane surface 24 is in contact with solution 14. Solution 20 has a composition substantially identical to that of solution 14, although the concentration of dicyanoaurate anions in solution 20 will be different from that in solution 14. The pH of solution 20 is in the range designated for solution 14.

Reference solution 20 contains reference electrode 34. This electrode may be formed from the same materials suitable for forming electrode 16 and may include chlorided terminal portion 27. The electrodes are each connected by connector wire to electrode potential measuring means 18 to form a circuit. Electrode potential measuring means 18 are also well-known in the art, e.g., a voltmeter or high impedance electrometers both perform such a function.

Membrane 26, having been formed as described above, has a surface area sufficient to permit the attachment of the membrane to a first opening 28 of reservoir 30. Reservoir 30 may be formed from the materials suitable for forming reservoir 12, and may be held above the interior bottom surface of reservoir 12 by bracket means, for example. The means of attachment of the membrane to first opening 28 is not critical and is typically accomplished by the use of a silicone rubber sealant 32 applied to the annular border of first opening 28. Second opening 36 of reservoir 30 is typically sealed by a stopper 38 during operation of the device, whereby electrode 34 communicates with potential measuring means 18 through a hole in stopper 38, as depicted in FIG. 1.

It will be apparent to those skilled in the art that the positions of the sample solution and reference solution may be reversed since each surface of membrane 26 is identical. Furthermore, in certain embodiments within the scope of the present invention, it may be desirable to minimize the effect of variations in chloride ion concentration. Thus, the device of FIG. 1 may further include an electrolyte bridge solution, known in the art, communicating with the sample solution via a liquid junction, as described in detail below in conjunction with the description of the alternative embodiment of FIG. 2.

Figure 2:
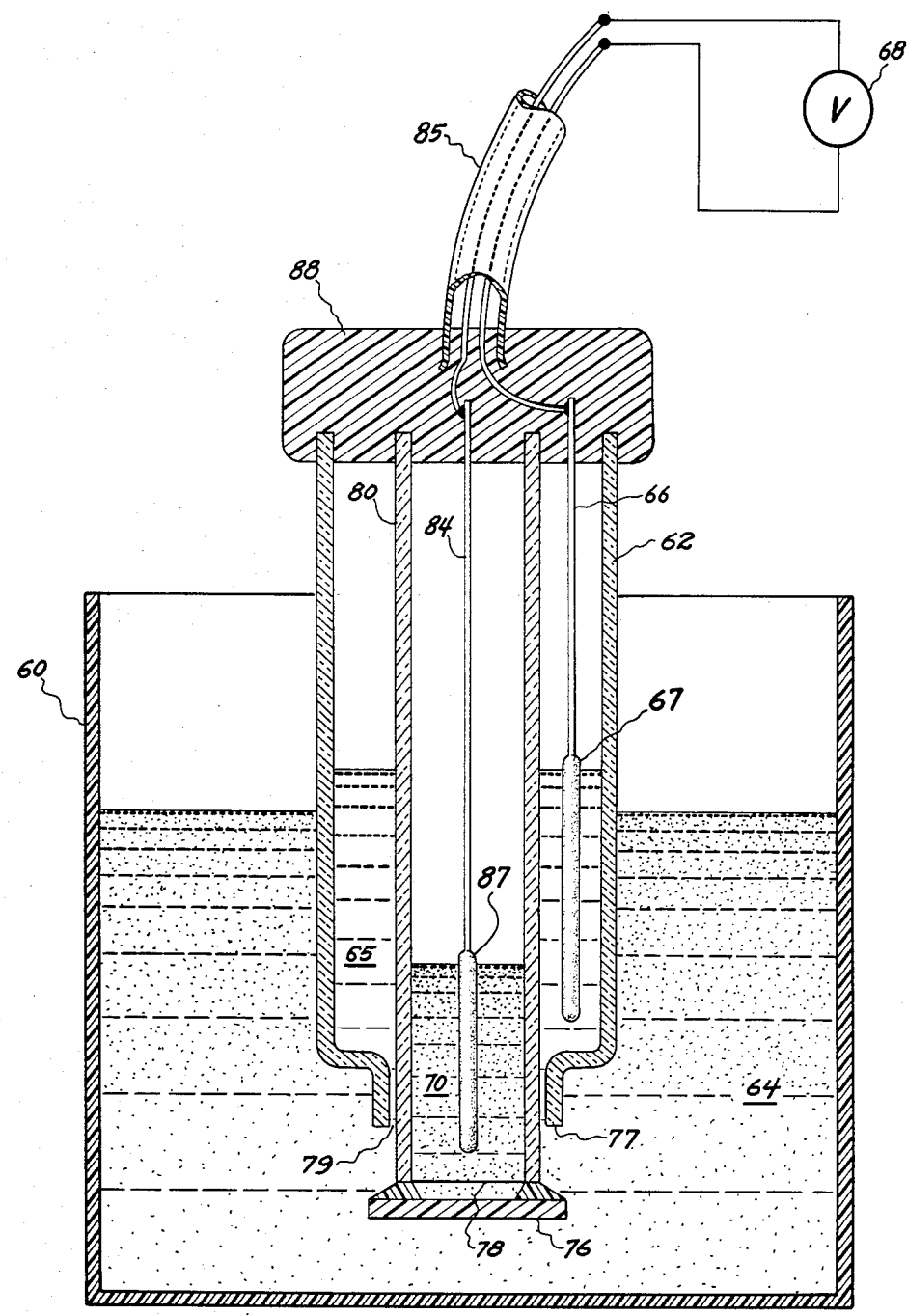
FIG. 2 is a sectional view of another embodiment of the device of the present invention.

An alternative embodiment of the device of the present invention is shown in FIG. 2. This particular apparatus will hereinafter also be referred to as a "combination device" because the first electrode and the reference electrode are contained within a unitary structure. Reservoir 62 contains therein a concentrated (about 2N to about 4N) aqueous electrolyte bridge solution 65 of potassium chloride. Reservoir opening 77 allows a liquid junction 79 to be formed between solution 65 and sample solution 64, the latter residing in reservoir 60. First electrode 66 may be formed from silver wire and may include a chlorided terminal portion 67 immersed in solution 65. Electrode 66 is connected by connector wire to electrode potential measuring means 68. The reservoirs may be formed from glass or other suitable dielectric materials as described above for the device of FIG. 1. Reservoir 80 contains aqueous reference solution 70 having dicyanoaurate ions contained therein. In addition to the dicyanoaurate anions, solutions 64 and 70 may contain the electrolytic components described above for the embodiment of FIG. 1. Reservoir 80 includes lower extremity 78 having adhesively attached thereto the semipermeable membrane 76 of the present invention. Reference electrode 84, comprised of any of the materials suitable for the other electrodes described herein, may include chlorided terminal portion 87 immersed in reference solution 70, and is connected to electrode potential measuring means 68 by a wire connector. The wire connectors for both electrodes 66 and 84 may be enclosed in a tubular insulating body 85. A cap 88 formed from a synthetic polymer or a ceramic material may be emplaced as shown in FIG. 2 to seal the upper extremities of reservoirs 62 and 80; and electrodes 66 and 84 may be connected to potential measuring means 68 through bores in the cap.

The use of an electrolyte bridge solution to minimize the effect of variations in the concentrations of various ions is shown in FIG. 2. Electrolyte bridge solution 65 contains chloride ions because the silver metal used to form first electrode 66 is chlorided. The potential value is dependent on the concentration of chloride ions in solution 65. Since the relatively narrow liquid junction 79 permits only very restricted mixing of sample solution 64 and bridge solution 65, the concentration of chloride ions in bridge solution 65 remains relatively constant and will not substantially vary from one sample solution to the next sample solution. Thus, in this embodiment of the present invention, the concentration of chloride ions in the sample solution need not be measured or controlled. Furthermore, the potential across liquid junction 79, while varying with the composition of the sample solution, is generally negligible, e.g., 1.0 millivolt or less, and can thus be ignored. Those skilled in the art understand that the embodiment of FIG. 1 may also include an electrolyte bridge solution in which electrode 16 would be immersed.

The device shown in FIG. 2 functions in the same manner as the device of FIG. 1, i.e., the potential difference across membrane 76 between solutions 64, 70 will be measured in order to calculate the unknown dicyanoaurate anion concentration in the sample solution. Furthermore, as in the embodiment of FIG. 1, the positions of the sample and reference solutions may be switched.

The method of the present invention may be carried out in conjunction with the membrane and device described above. Thus, the concentration of dicyanoaurate anions in a solution may be determined by measuring the potential between a first electrode in contact with a first solution having an unknown concentration of dicyanoaurate anions and a second electrode in contact with a reference solution having a known concentration of dicyanoaurate anions, said solutions each having a pH between about 4 and 11 and separated by an elastomeric membrane as described above. As also described above, the reference solution contains a known concentration of dicyanoaurate anions, while the sample solution contains an unknown concentration of the same anions. It has been discovered that the potential difference across the membrane of the present invention is proportional to the logarithm of the ratio of the concentration of dicyanoaurate anions in the sample solution to the concentration of dicyanoaurate anions in the reference solution. Thus, since the graphic relationship between the measured potential and the concentration of dicyanoaurate anions in the sample solution conforms to the relationship predicted by the well-known Nernst equation, determination of the potential difference by the method of the present invention allows the ready determination of the concentration of dicyanoaurate anions contained in the sample solution.

In practicing the method of the present invention, a supporting electrolyte such as $K_2SO_4$ may be added to the sample solution at levels ranging from about 0.1 M to about 1.0 M. The supporting electrolyte is added to dilute the sample solution in order to minimize variations in the activity coefficient of the dicyanoaurate anion in the sample solution. A pH buffer is also included in the sample solution in order to maintain the pH between about 4 and 11. These additional components are also added to the reference solution. If the electrode immersed in the sample solution is simply a chlorided silver wire, then a source of chloride ions, such as potassium chloride, is also added to the sample solution at a concentration of about 1.0 mM or higher. Furthermore, if the device of the present invention does not include the electrolyte bridge solution described above, the chloride ion concentration must be measured for each sample solution being tested, because variations in the chloride ion concentration may affect the potential difference value. The chloride ion concentration may be measured by well-known analytical methods, e.g., precipitation or atomic absorption.

The following specific examples describe novel embodiments of the present invention. They are intended for illustrative purposes only and should not be construed as a limitation upon the broadest aspects of the invention.

EXAMPLE 1

Sensor devices and membranes of the present invention were tested for electrochemical response, i.e., the sensitivity of the device to changes in the concentration of the cation or anion under investigation. An ideal electrochemical response is generally indicated when a ten-fold change in ion concentration at about 24° C. results in a change in potential of about 59.6 mV.

Two devices designated as A and B and substantially identical to those shown in FIG. 1 were constructed in the manner described above. The reservoirs of each device were made of glass. The reference solution contained 1.0 mM $KAu(CN)_2$; 100.0 mM $K_2SO_4$; 10.0 mM KCl; and one Beckman pH buffer capsule (pH 10.01) per liter of solution. Sample solutions 1-4 contained 100.0 mM $K_2SO_4$; one Beckman (pH 10.0) buffer capsule; and the appropriate concentration of $Au(CN)_2^-$ listed in Table I below. The aqueous solutions in each device were maintained at a temperature of about 24° C.

The sample and reference solutions were connected to a voltmeter by chlorided silver wire electrodes. Emplacement of the reservoir containing the reference solution in the sample-containing reservoir brought about an immediate steady state potential, i.e. a potential value reading on the voltmeter in less than one minute. After each potential was obtained, the devices were rinsed and dried prior to immersion in the next sample solution. The potential value data obtained in Example 1 is set forth in Table I and shown graphically in FIG. 3, in which curve A represents data for device A, curve B represents data for device B, and curve E represents the electrochemical response predicted by the Nernst equation.

TABLE 1

| Sample No. | [Au(CN)$_2$$^-$] (mM) | Potential (mV) Device A | Potential (mV) Device B |
|---|---|---|---|
| 1 | 10.0 | −64.4 | — |
| 2 | 1.0 | −6.5 | −6.5 |
| 3 | 0.1 | 50.3 | 49.5 |
| 4 | 0.01 | 101.0 | 98.3 |

The above figures indicate that the potential-concentration response resulting from the device of the present invention was excellent at dicyanoaurate anion concentrations of 0.1 mM or above. Although the potential-concentration response decreased at concentrations lower than 1.0 mM, the response was still sufficient to permit the measurement of ion concentrations as low as 0.1 mM. The potential-concentration response shown in Table I is equal to the response exhibited in ion-selective devices of the prior art.

Furthermore, Table I demonstrates reproducible potential-concentration response data when multiple devices (device A and device B) of the present invention are used.

Moreover, the membranes of the present invention exhibited unexpectedly low electrical resistance: $1.0 \times 10^5$ ohms and $6.0 \times 10^4$ ohms for devices A and B, respectively. These low resistances obviate the use of cumbersome and expensive electrical shielding which is typically required to reduce electrical interference in the vicinity of prior art ion-selective devices. Furthermore, the low resistances eliminate the need for high-input-impedance electrometers.

Figure 3:
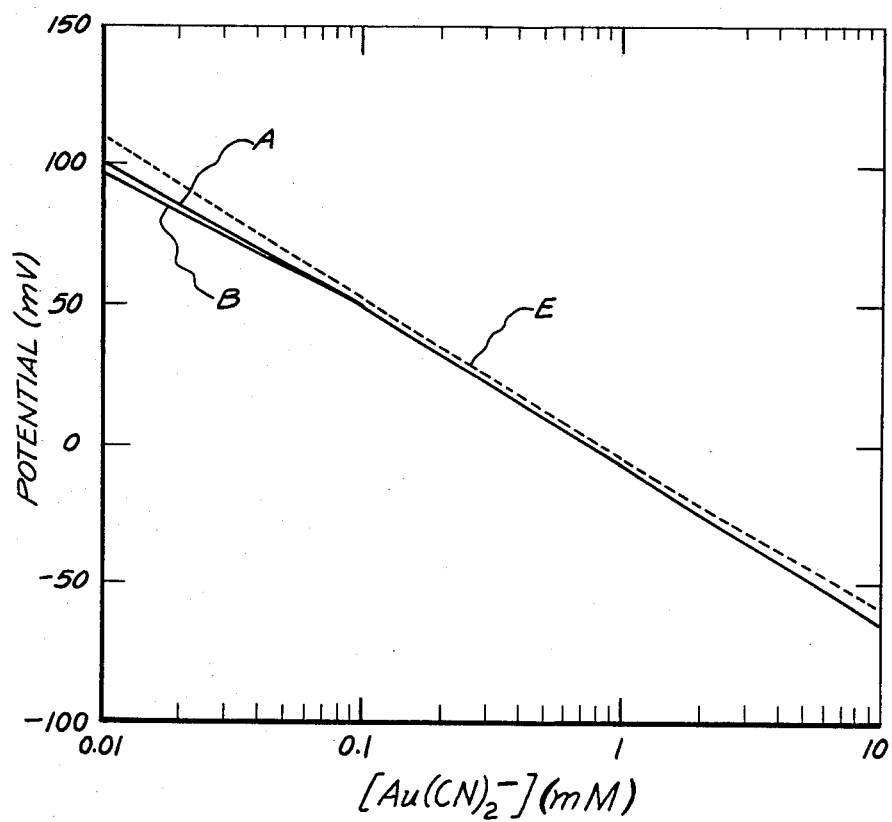
FIG. 3 is a graph depicting the relationship between potential difference and ion concentration for sample solutions tested with devices such as those depicted in FIG. 1.

FIG. 3 graphically depicts the potential-concentration response data of Example 1 as compared to the response predicted by the Nernst equation (Curve E). It is clear from FIG. 3 that the membranes and devices of the present invention result in a near-perfect correlation between experimentally determined potential-concentration relationships and theoretical potential-concentration relationships.

EXAMPLE 2

Device C, substantially identical to that depicted in FIG. 2 (i.e., a combination device) was constructed as described above. The reservoirs were formed from glass tubes. The aqueous solution contained 1.0 mM $KAu(CN)_2$; 100 mM $K_2SO_4$, 10 mM KCl; and one Beckman pH 10.01 buffer capsule per liter of solution. The electrolyte bridge solution contained 3N KCl. Chlorided silver wire reference electrodes were immersed in both the KCl solution and the reference solution; each was connected by wire connectors to a voltmeter. Five different aqueous solutions (i.e., sample solutions) were individually tested, each at both a pH of 8.0 and a pH of 10.0. Each solution contained 100 mM $K_2SO_4$ and a particular concentration of $KAu(CN)_2$, as listed below in Table II. Commercial buffering agents were used to adjust the pH to the designated level.

A membrane as described above was glued to the bottom opening of device C, and a molded plastic cap sealed the top of the device. The device (containing the reference solution and the 3N KCl solution) was immersed in each sample solution as depicted in FIG. 2.

A steady state potential for each sample was obtained in less than a minute. After each potential was obtained, the device was rinsed and dried prior to immersion in the next sample solution. The results obtained are shown in Table II:

TABLE II

| Sample No. | [Au(CN)$_2^-$] (mM) | pH | Potential (mV) Device C |
|---|---|---|---|
| 5 | 10.1 | 8.0 | 79.8 |
| 5 | 10.1 | 10.0 | 75.6 |
| 6 | 1.0 | 8.0 | 138.0 |
| 6 | 1.0 | 10.0 | 134.3 |
| 7 | 0.1 | 8.0 | 195.9 |
| 7 | 0.1 | 10.0 | 190.7 |
| 8 | 0.01 | 8.0 | 249.1 |
| 8 | 0.01 | 10.0 | 238.8 |
| 9 | 0.001 | 8.0 | 282.2 |
| 9 | 0.001 | 10.0 | 271.8 |

Figure 4:
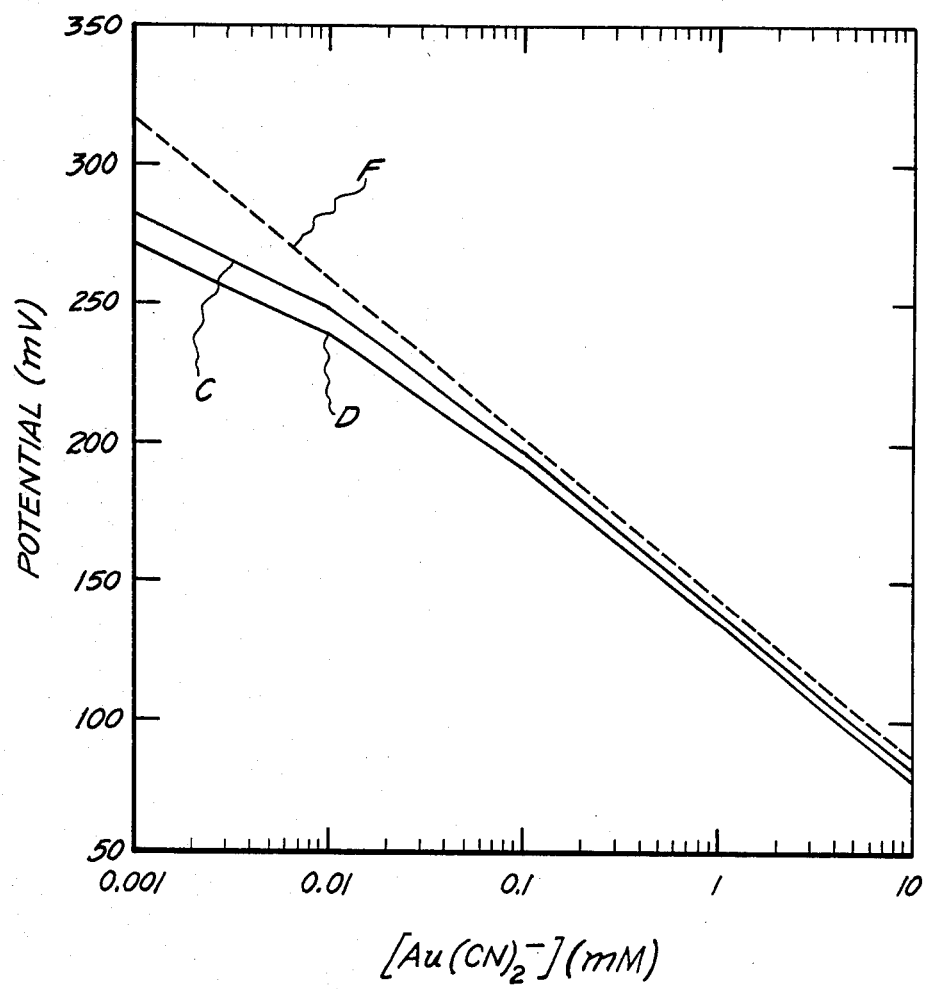
FIG. 4 is a graph depicting the relationship between potential difference and ion concentration for sample solutions tested with devices such as those depicted in FIG. 2.

The above figures indicate that the potential-concentration response resulting from the combination device of the present invention was generally excellent. FIG. 4 is a graphical representation of the data of Table II, wherein Curves C and D correspond to values obtained for solutions at pH 8.0 and pH 10.0, respectively. Curve F represents the theoretical slope of 59.6 mV, as predicted by the Nernst equation. Table II and FIG. 4 both demonstrate that a variation in the pH of the sample solution has no appreciable effect on the potential value.

The metal ionic complex-selectivity of the membranes of devices A, B and C for Au(CN)$_2^-$ anions was excellent. For example, the presence of nickel tetracyanoaurate (Ni(CN)$_4^{-2}$) anions in sample solutions having Au(CN)$_2^-$ anion concentrations in the range of 0.1 mM to 1.0 mM did not interfere with the determination of the Au(CN)$_2^-$ anion concentration, even when the ratio of Ni(CN)$_4^{-2}$ anions to Au(CN)$_2^-$ anions was as high as 100:1.

While the invention has been described with respect to preferred embodiments, it will be apparent that certain modifications and changes can be made without departing from the spirit and scope of the invention and, therefore, it is intended that the foregoing disclosure be limited only by the claims appended hereto.

What is claimed is:

1. A semipermeable membrane for determining the concentration of dicyanoaurate anions in a solution, said membrane comprising an organopolysiloxane-polycarbonate block copolymer film permeable to dicyanoaurate anions and a complexed salt of the dicyanoaurate anion, said block copolymer having a dielectric constant of from about 4 to about 13.

2. The membrane of claim 1 wherein the complexed salt includes a cationic radical comprising a plurality of phenyl groups bonded to an electron-accepting atom.

3. The membrane of claim 2 wherein the cationic radical of the complexed salt is a tetraphenyl radical.

4. The membrane of claim 3 wherein the electron-accepting atom is selected from the group consisting of phosphorus and arsenic.

5. The membrane of claim 4 wherein the cationic radical of the complexed salt is a tetraphenylphosphonium radical.

6. The membrane of claim 4 wherein the cationic radical of the complexed salt is a tetraphenylarsonium radical.

7. A method for determining the concentration of dicyanoaurate anions in an aqueous solution, said method comprising measuring the potential between a first electrode in contact with a first solution having an unknown concentration of dicyanoaurate anions and a second electrode in contact with a reference solution having a known concentration of dicyanoaurate anions, said solutions each having a pH between about 4 and 11 and separated by a membrane comprising an organopolysiloxane-polycarbonate block copolymer film permeable to dicyanoaurate anions and a complexed salt of the dicyanoaurate anion, said block copolymer having a dielectric constant of from about 4 to about 13.

8. A device for determining the concentration of dicyanoaurate anions in a sample solution containing an unknown concentration of dicyanoaurate anions and having a pH between about 4 and 11, said device comprising a reference electrode immersed in a reference solution containing a known concentration of dicyanoaurate anions and a second electrode adapted to be immersed in said sample solution, said reference solution having a pH between about 4 and 11, and further comprising a semipermeable membrane adapted to separate said reference solution from said sample solution, said membrane formed from an organopolysiloxane-polycarbonate block copolymer film permeable to dicyanoaurate anions and a complexed salt of the dicyanoaurate anion, said block copolymer having a dielectric constant of from about 4 to about 13, and means present to connect said electrodes by an external circuit, including potential measuring means.

* * * * *